US00PP22389P2

(12) United States Plant Patent
Kaagman

(10) Patent No.: US PP22,389 P2
(45) Date of Patent: Dec. 20, 2011

(54) ***OSTEOSPERMUM* PLANT NAMED 'TRA WHIT'**

(50) Latin Name: *Osteospermum ecklonis*
Varietal Denomination: Tra Whit

(75) Inventor: Pim Kaagman, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 206 days.

(21) Appl. No.: 12/657,232

(22) Filed: Jan. 15, 2010

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP20,270 P2 * 9/2009 Laughner ..... Plt./360

OTHER PUBLICATIONS

UPOV ROM GTITM Computer Database, GTI Jouve Retrieval Software 2011/01 Citation for 'Tra Whit'.*

* cited by examiner

*Primary Examiner* — Wendy C Haas
(74) *Attorney, Agent, or Firm* — S. Matthew Edwards

(57) ABSTRACT

A new *Osteospermum* plant named 'Tra Whit,' particularly distinguished by the medium to large white ray florets, early flowering habit, compact and upright plant habit with green leaves and excellent branching.

1 Drawing Sheet

Latin name of the genus and species of the plant claimed: *Osteospermum ecklonis.*

Varietal denomination: 'Tra Whit'.

BACKGROUND OF THE NEW PLANT

The present invention comprises a new *Osteospermum*, botanically known as *Osteospermum ecklonis*, and hereinafter referred to by the variety name 'Tra Whit.'

'Tra Whit' is a product of a planned breeding program. The new cultivar has medium to large white ray florets, early flowering habit, compact and upright plant habit with green leaves and excellent branching.

'Tra Whit' originated from a hybridization made in July 2006 in a controlled breeding environment in Andijk, Netherlands. The seed was sown in September 2006. The female parent was the proprietary plant designated 'O03-20-2,' unpatented, with light purple flower color. 'O03-20-2' has less vigorousness and smaller flowers than 'Tra Whit.'

The male parent of 'Tra Whit' was a proprietary plant designated as 'O03-6-1,' unpatented, with white and blue eyed flowers. 'O03-6-1' has smaller flowers and less vigor than 'Tra Whit.'

'Tra Whit' was selected as one flowering plant within the progeny of the stated cross in January 2007 in a controlled environment in Andijk, Netherlands.

The first act of asexual reproduction of 'Tra Whit' was accomplished when terminal cuttings were propagated from the initial selection in January 2007 in a controlled environment in Andijk, Netherlands.

BRIEF SUMMARY OF INVENTION

Horticultural examination of plants grown from the cuttings of the plant initiated in January 2007, and continuing thereafter, has demonstrated that the combination of characteristics as herein disclosed for 'Tra Whit' are firmly fixed and are retained through successive generations of asexual reproduction.

'Tra Whit' has not been observed under all possible environmental conditions. The phenotype may vary significantly with variations in environment such as temperature, light intensity and day length.

A Plant Breeder's Right for this cultivar was applied for in Canada on Jan. 30, 2009. 'Tra Whit' has not been made publicly available more than one year prior to the filing of this application.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

The accompanying photographic drawings show typical flower and foliage characteristics of 'Tra Whit' with colors being as true as possible with an illustration of this type.

Figure 1:
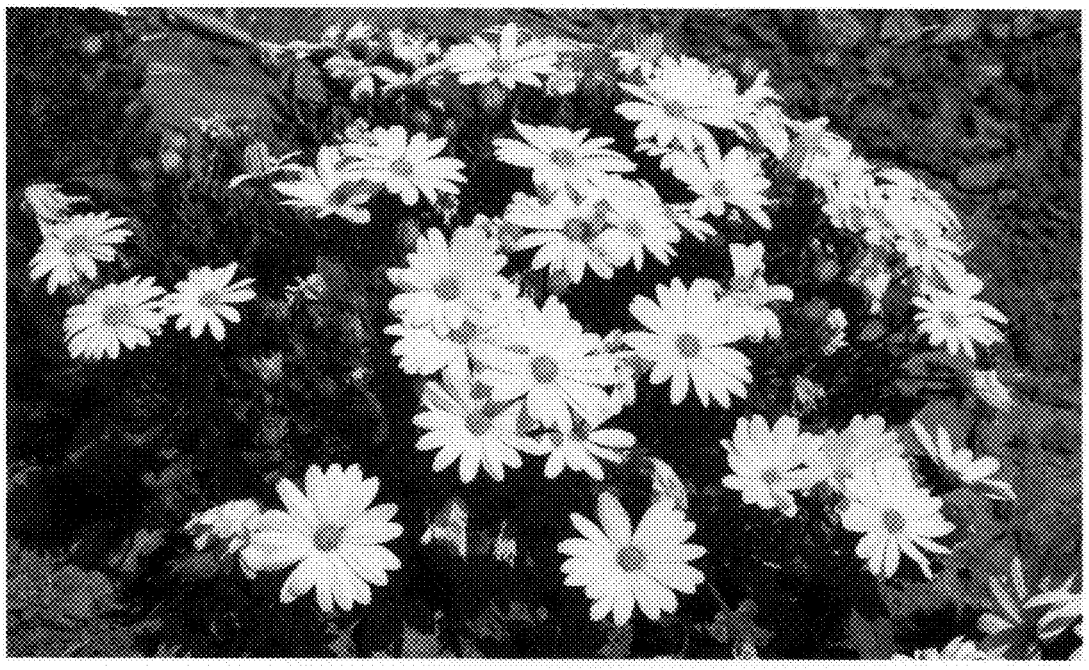
Figure 2:
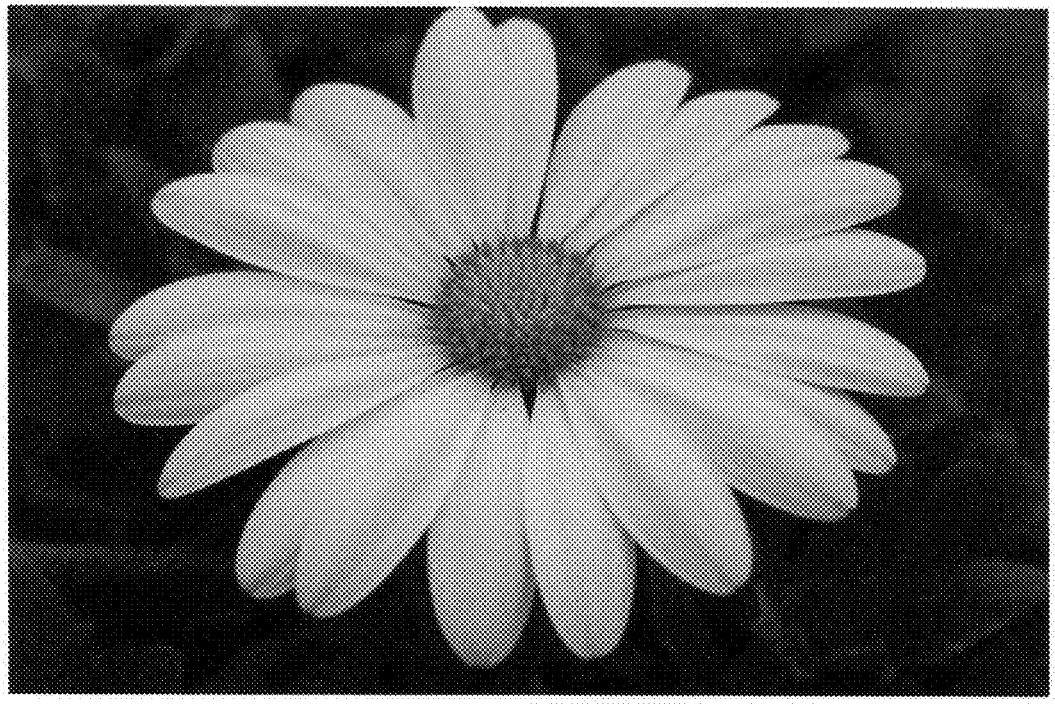

The photographic drawings show in FIG. 1, a flowering plant of the new variety growing in a outdoor field trial in Gilroy, Calif. in the summer of 2009, and in FIG. 2, a close-up of the flowers.

DETAILED BOTANICAL DESCRIPTION

The plant descriptions and measurements were taken in Salinas, Calif. in the summer of 2009 under natural light. These plants were started and grown in Gilroy, Calif., and then planted into the outdoor garden in Salinas. Plants were approximately 8-9 months old.

Color references are made to The Royal Horticultural Society Colour Chart (R.H.S.) 2001.

TABLE 1

DIFFERENCES BETWEEN THE NEW VARIETY 'TRA WHIT' AND A SIMILAR VARIETY

| | 'Tra Whit' | 'Balserilla' (U.S. Plant Pat. No. 20,270) |
|---|---|---|
| Flower size: | Larger | Smaller |
| Habit: | More compact | Less compact |

Plant:
- *Form, growth and habit.*—Compact, semi-upright and mounded plant habit. Vigorous habit.
- *Plant height.*—23-25 cm.
- *Plant height (inflorescence included).*—32-35 cm.
- *Plant width.*—45-48 cm.
- *Garden performance and tolerance to weather.*—Very good.
- *Crop time to flowering.*—About 10 weeks.

Roots:
- *Number of days to initiate and produce roots.*—24-27 days at about 22 degrees C.
- *Type.*—Fine, fibrous, free branching.
- *Color.*—RHS N155B but whiter.

Foliage:
- *Arrangement.*—Alternate.
- *Immature, leaf color, upper surface.*—Closest to RHS 137A but more yellow.
- *Lower surface.*—Closest to RHS 138B.
- *Mature, leaf color, upper surface.*—Closest to RHS 137A but slightly more yellow and darker than the immature.
- *Lower surface.*—Closest to RHS 138B.
- *Length.*—4.5-4.7 cm.
- *Width.*—1.7-2.4 cm.
- *Shape.*—Elliptical.
- *Base shape.*—Attenuate.
- *Apex shape.*—Acute.
- *Margin.*—Slightly serrate.
- *Texture, upper surface.*—Hirsute.
- *Lower surface.*—Hirsute.
- *Color of veins, upper surface.*—RHS 144B.
- *Color of veins, lower surface.*—RHS 144B.
- *Petiole color.*—RHS 144B.
- *Length.*—0.3 cm.
- *Diameter.*—0.4 cm.
- *Texture.*—Hirsute.

Stem:
- *Quantity of main branches per plant.*—About 10.
- *Color of stem.*—RHS 144B.
- *Length of stem.*—26-29 cm.
- *Diameter.*—0.3-0.5 cm.
- *Length of internodes.*—0.5-1.0 cm.
- *Texture.*—Glabrous.
- *Color of peduncle.*—RHS 144A.
- *Length of peduncle.*—8-10.5 cm.
- *Peduncle diameter.*—0.2 cm.
- *Texture.*—Hirsute.

Inflorescence:
- *Type.*—Daisy-type inflorescence form, held above the foliage, arising from leaf axis. Disc and ray florets developing acropetally on a capitulum. Freely flowering habit, numerous inflorescences develop over time per plant.
- *Quantity of inflorescences per plant.*—15-18.
- *Lastingness of individual blooms on the plant.*—11-14 days.
- *Fragrance.*—None.

Bud (just when starting to show color):
- *Color.*—RHS 151B.
- *Length.*—1.5-1.7 cm.
- *Width.*—0.8-0.9 cm.
- *Shape.*—Oblate.

Immature inflorescence:
- *Diameter.*—4.5 cm.
- *Color of ray florets, upper surface.*—RHS 155D but creamier white.
- *Lower surface.*—RHS 155C ground color suffused with RHS 8D mid veins and RHS 9B apex.

Mature inflorescence:
- *Diameter.*—6-6.5 cm.
- *Depth.*—0.5-1.0 cm.
- *Total diameter of 'disc'.*—1.0-1.1 cm.

Ray florets:
- *Average quantity of florets.*—16-18 in several whorls.
- *Color of florets, upper surface.*—RHS 155D but creamier white.
- *Lower surface.*—RHS 155C suffused with RHS 8D mid veins and RHS 9B apex.
- *Length.*—3.0-3.2 cm.
- *Width.*—0.9-1.0 cm.
- *Shape.*—Obovate.
- *Apex shape.*—Praemorse.
- *Margin.*—Entire.
- *Texture, upper surface.*—Papillose; long lanate covering the tube base.
- *Lower surface.*—Papillose; long lanate covering the tube base.

Disc florets:
- *Average quantity of florets.*—About 100.
- *Color of florets.*—RHS 155D but whiter.
- *Length.*—0.5-0.6 cm.
- *Width.*—0.55 cm.
- *Shape.*—Tubular, elongated.
- *Apex shape.*—Acute, 5 pointed.
- *Margin.*—Entire.

Phyllaries:
- *Quantity.*—14-18.
- *Color, upper surface.*—RHS 146B.
- *Lower surface.*—RHS 146B.
- *Length.*—0.3-0.65 cm.
- *Width.*—0.05-0.1 cm.
- *Shape.*—Lanceolate.
- *Apex shape.*—Acute.
- *Based.*—Fused.
- *Margins.*—Entire.
- *Texture, upper surface.*—Smooth.
- *Lower surface.*—Scabrous.

Reproductive organs;
- *Gynoecium.*—Found on both florets.
- *Pistil.*—1.
- *Length.*—0.8 cm.
- *Style color.*—About RHS 145A.
- *Style length.*—0.5 cm.
- *Stigma color.*—Close to RHS 200A.
- *Androecium.*—Found on only disc florets.
- *Stamens.*—About 5.
- *Color of filaments.*—RHS 155D but whiter.
- *Length filaments.*—0.3-0.4 cm.
- *Anther color.*—Close to RHS N199B.
- *Anther length.*—0.5 cm.
- *Anther shape.*—Oblong.

*Color of pollen.*—About RHS 24B.

*Pollen amount.*—Abundant.

*Fertility/seed set.*—Has not been observed on this hybrid.

Disease/pest resistance: Disease/pest resistance has not been observed on this hybrid.

What is claimed is:

1. A new and distinct variety of *Osteospermum* plant named 'Tra Whit,' substantially as illustrated and described herein.

* * * * *